United States Patent [19]

Ketchum, Jr.

[11] Patent Number: 4,908,025
[45] Date of Patent: Mar. 13, 1990

[54] BODY WASTE RECEPTOR FOR BED PATIENTS

[76] Inventor: Joseph W. Ketchum, Jr., 13751 St. Andrews Dr. No. 36E, Seal Beach, Calif. 90740

[21] Appl. No.: 861,586

[22] Filed: May 9, 1986

[51] Int. Cl.⁴ .............................................. A61M 1/00
[52] U.S. Cl. ...................................... 604/327; 4/144.3
[58] Field of Search ................................ 604/327–331, 604/348–355, 346, 356, 386, 393, 394, 402; 4/144.1–144.4; 248/95

[56] References Cited

U.S. PATENT DOCUMENTS 3,405,714 10/1968 Moss ................................... 604/353
3,755,989 5/1971 Anderson ........................... 604/348

FOREIGN PATENT DOCUMENTS 1236346 6/1960 France ................................ 4/144.3

Primary Examiner—J. L. Kruter
Attorney, Agent, or Firm—John E. Wagner

[57] ABSTRACT

A body waste receptor for application to a bed patient lying on one side including an open frame of lightweight tubular material provided to hold and keep in place a disposable bag and straps for embracing the waist and thighs of a patient, thus holding the frame and bag in place against the patient.

8 Claims, 7 Drawing Sheets

BODY WASTE RECEPTOR FOR BED PATIENTS

The present invention relates to appliances, of which bed pans are a well known example, for receiving the body wastes of bed patients for conveyance to a disposal site.

The inconvenience and discomfort associated with the use of conventional bed pans has led to attempts to devise various appliances for ameliorating the conditions connected with their use, such as disposable linings. However, patients who require such appliances are forced to sit or lie in a relatively fixed and uncomfortable position on them until relieved by an attendant after a frequently prolonged wait. It is a primary object of the present invention to provide an appliance of the same class which will eliminate the discomfort of having to sit or lie upon an object during its use and which will at the same time be conveniently accessible to an attendant removing and replacing it. Likewise, it is an object to provide an easily disposable body waste receptacle.

SUMMARY OF THE INVENTION

According to the present invention an appliance is provided which is attachable to the patient by flexible belts while he is lying in bed on one side instead of in a supine posture. The appliance comprises a semi-rigid, generally oval, frame of metal or plastic to which belts may be releasably attached so that, following attachment of the open end of a disposable bag to the frame, it may be held in place on the patient's body by the belts. Upon release of the belts, the frame and bag may be conveniently carried to a receptacle such as a plastic waste basket at the bedside for transportation to a toilet or other disposal site. The belts are not necessarily attached to the frame. The belts may be one piece belts placed completely and securely around the patient's waist and thighs, and then the frames, with slightly reversed curves away from the body at each end or with end guards, may be inserted under the already in place belts.

DETAILED DESCRIPTION OF THE PREFERRED EMBODIMENT

Figures 1, 1A, 2, 3, 4, 5, 6:
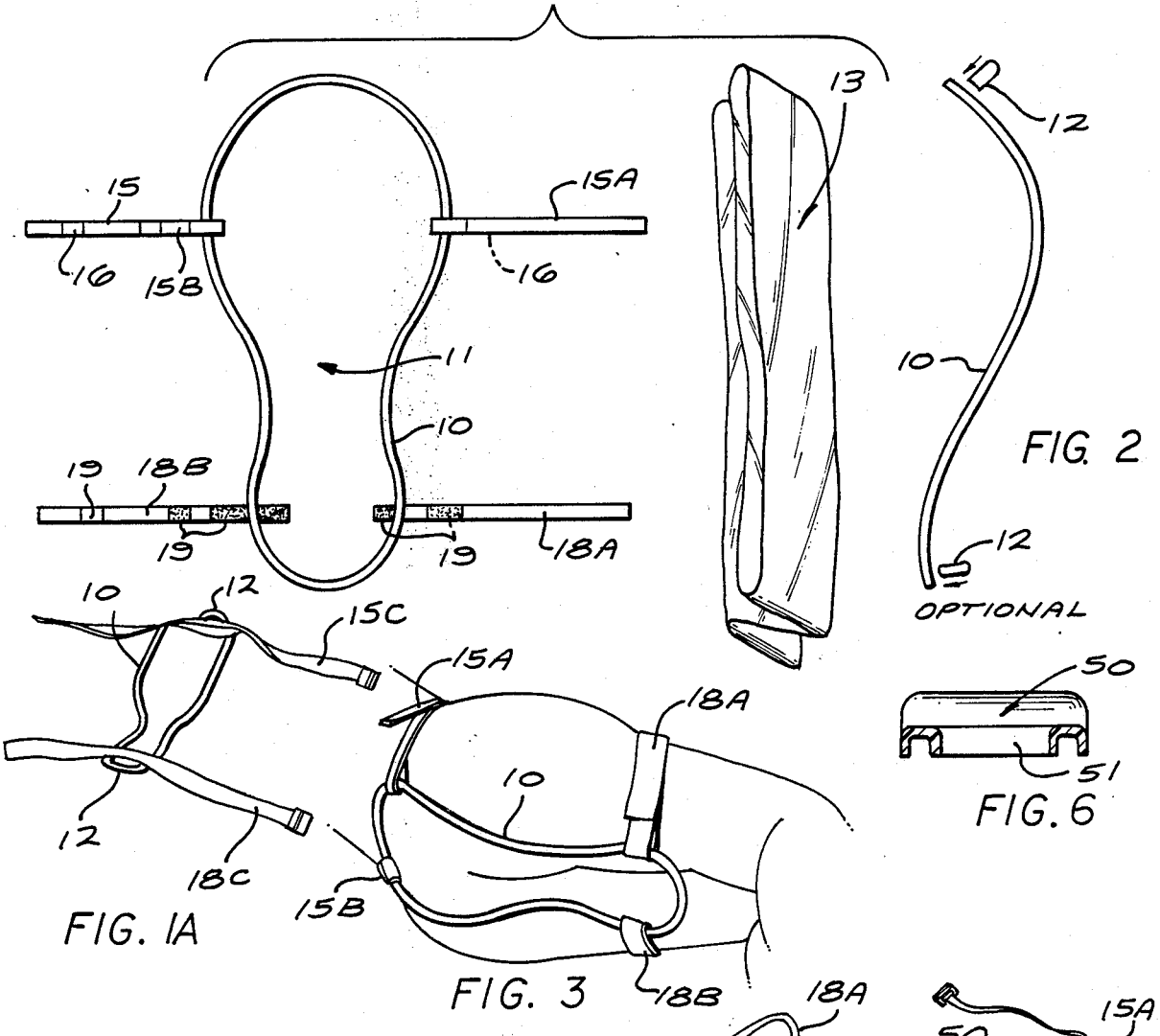
FIG. 1 is a view in plan of the frame, collection bag and belts of the present invention.
FIG. 1A is a perspective view of another embodiment of this invention employing two rather than four straps and end hook strap retainers.
FIG. 2 is a view in side elevation of the frame of this invention showing its curvature to conform to body outline.
FIG. 3 is a view in perspective of the frame and belts attached to the body of a patient, only a portion of which is shown, and with the bag removed to show more clearly the manner of employment of the appliance.
FIG. 4 is a view in side elevation and partly in section of the frame and bag following their removal to a waste basket, shown in section.
FIG. 5 is a perspective view of this invention with the frame formed of plastic.
FIG. 6 is a vertical sectional view of the frame of FIG. 5 taken along lines 6—6 of FIG. 5.

As shown in the drawing, the appliance of the present invention comprises a frame 10 having an open interior 11 and which may conveniently be formed of metal or plastic tubing into the generally oval body-conforming shape shown in FIGS. 1 and 2. The frame 10 is configured for engagement with and holding the upper edge of the open end of a disposable bag 13 which is provided for the reception of the patient's body wastes.

A pair of upper straps 15A and 15B are each provided with patches of self-adhering material 16, such as the hook and pile fabric commonly identified as Velcro, by means of which each strap 15 may be attached to the frame 10 by wrapping around the same and adhering to itself. Similarly, a pair of lower straps 18A and 18B are each provided with patches 19 of such hook and pile material uncoupled for removably securing the lower straps 18A and 18B around the thighs of a patient as shown in FIG. 3.

FIG. 1A shows an alternate form of this invention in which the frame 10 has a pair of end guards 12 for holding the straps 15C and 18C from slipping off of the end of the frame 10. The guards 12 are upstanding loops which act as belt retainers. They may also be seen as optional attachments to the frame 10 as shown in FIG. 2. They may be secured to the frame 10 by brazing, by screws or other fastners, or, if frame 10 is molded of plastic, as integral parts.

The appliance of this invention is employed for its intended purpose by first securing a disposable plastic bag 13 to the frame 10 or be positioning it with the open end of the bag 13 positioned filling the interior opening of the frame 10. The straps 15 an 18 are attached to the frame 10 as has been described above, and the frame 10 is then positioned against the body of the patient, as shown in FIG. 3, with the bag lying on the bed alongside the patient. When the appliance is so attached and the straps 15 and 18 are comfortably tight, the patient, by raising his knees, can bring the frame closer to his body, insuring a fluid tight contact with the patient. The frame is slightly flexible and generally seat shaped to conform to the rear of the patient when his knees are slightly drawn up.

The feature of FIGS. 15D and 18D allows the attendant to first attach the belts to the patient's body and then apply the frame 10 and bag 13 by slipping the end guards 12 at each end of the frame 10 under the already attached belts 15D and 18D.

In either case, the soiled bag 13 may be easily removed without disturbing the patient by disengaging the straps 15 and 18 from the patient's body and carrying the frame 10 and bag 13 together to a suitable receptacle such as plastic waste basket 20, as shown in FIG. 4, following which the frame 10 may be removed and the basket and its contents disposed of.

In FIG. 5 a plastic frame 50 is shown in the order of 1/16 to ⅛ inch thick with an edge rim 51 and slightly flexible, defining an elongated waste receiving opening 52 through which a bag 13 extends and overlies the front surface 52 of the frame 50. The closed end 13A of the bag 13 extends below the plastic frame 50 for receiving body waste.

The plastic form of this invention has an advantage over the metal tubing of lower cost and can easily provide integral means for holding straps 15 and 18 in place. These integral means can be minor end reentrant portions 55 and 56 or integral slots 60–63. The straps 53 and 54 passing through respective slots 60 and 62 for strap 53, and 61 and 63 for strap 54 are trapped and cannot slide off the frame. Also, the straps 15 and 18 can trap the bag 13 portions within the slots to hold the bag from unintended disengagement with the frame 50.

Altogether we have devised a waste removal device which secures to a patient lying on his side with minimum discomfort or embarrassment to the patient normally covered with bed clothes. It also can be used on an incontinent patient or one who may not fully cooperate with the attendant. Employing this invention the attendant can determine when the appliance has been used and remove it with little or no disturbance of the patient.

Another application which should receive wide acceptance is the use of this device for giving enemas. By attaching a slightly deeper bag and snipping a small hole in the plastic just below the uppermost side of the frame, the enema tube may be inserted through this hole and from there into the patient's rectum, the entire operation easily observed through the clear plastic.

The extreme flexibility of the bag makes it possible to easily grasp the enema tube from outside the bag, using the slack material therein to maneuver.

After completing the enema, the tube is then pulled back out through the small hole in the bag and the bag is still undisturbed in place to easily catch all the resultant waste and water.

While the preferred embodiment of the invention has been shown and described herein, it will be understood that variations in the appliance and manner of its use will occur to users of such appliances. The invention is not to be considered as limited to the form herein disclosed except as required by the prior art and the spirit of the appended claims.

What is claimed is:

1. An appliance for use on a bed confined patient reclining in a side posture, in place of a bed pan, comprising a semi-rigid generally oval frame having an upper portion shaped to lie closely adjacent the rear of the waist of a person and a lower portion shaped to lie closely adjacent the rear of the thighs of such person and having an open interior, means for removably attaching to said frame a disposable bag, and means for releasably connecting said frame, together with a bag attached thereto, to the rear of the waist and thighs of a person comprising a first belt means carried by said upper portion of said frame, for encircling the waist of such person, and a second belt means carried by said lower portion of said frame for encircling the thighs of such person between the knees and crotch, whereby, when the appliance is so attached, raising of the person's knees will press the said upper portion of said frame more closely against the rear of such person.

2. An appliance for use on a bed confined patient reclining in a side posture, in place of a bedpan comprising:
a frame defining an opening for receiving waste;
said frame including side portions defining said opening and having a generally seat-shaped bend generally conforming to the hip and upper legs of a person with the legs partially drawn up;
disposable waste collection means securable in said opening;
a first means engaging said frame and encircling the waist of the patient; and
a second means engaging said frame and encircling the thighs of said patient to hold the appliance to the patient and press said frame more closely against the patient when his knees are raised.

3. An appliance in accordance with claim 2 wherein said second means comprises a pair of straps in longitudinally spaced engagement with said frame for compressing said frame and disposable waste collection means against the body of the patient.

4. An appliance in accordance with claim 3 in which said frame is formed of plastic with integral notches for engaging said straps.

5. An appliance in accordance with claim 2 wherein said frame is slightly flexible whereby said second means can cause slight deformation of said frame to conform to the body of the patient.

6. An appliance in accordance with claim 5 in which said frame is a continuous tube of metal.

7. An appliance in accordance with claim 5 in which said frame includes means for securing said disposable waste collection means thereto.

8. An appliance in accordance with claim 2 wherein said disposable waste collection means comprises a plastic bag.

* * * * *